(12) United States Patent
Nagai et al.

(10) Patent No.: US 7,553,624 B2
(45) Date of Patent: Jun. 30, 2009

(54) METHOD OF ANALYZING PHYSIOLOGICAL FUNCTION OF TARGET SUBSTANCE

(75) Inventors: Takeharu Nagai, Tokyo (JP); Atsushi Miyawaki, Saitama (JP)

(73) Assignee: Japan Science & Technology Agency, Kawaguchi-Shi Saitama (JP)

( * ) Notice: Subject to any disclaimer, the term of this patent is extended or adjusted under 35 U.S.C. 154(b) by 0 days.

(21) Appl. No.: 10/557,906

(22) PCT Filed: May 20, 2004

(86) PCT No.: PCT/JP2004/007238

§ 371 (c)(1),
(2), (4) Date: Jan. 9, 2007

(87) PCT Pub. No.: WO2004/104583

PCT Pub. Date: Dec. 2, 2004

(65) Prior Publication Data

US 2007/0161636 A1    Jul. 12, 2007

(30) Foreign Application Priority Data

May 21, 2003    (JP)    ............................. 2003-143932

(51) Int. Cl.
| | |
|---|---|
| C12Q 1/68 | (2006.01) |
| C12Q 1/70 | (2006.01) |
| G01N 33/53 | (2006.01) |
| C07H 19/04 | (2006.01) |
| C07H 21/02 | (2006.01) |

(52) U.S. Cl. .................. 435/6; 435/5; 435/7.1; 435/7.2; 536/23; 536/24.3; 536/26.6

(58) Field of Classification Search ............ 435/6, 435/5, 7.1, 7.2; 536/26.6, 23.1, 24.3
See application file for complete search history.

(56) References Cited

U.S. PATENT DOCUMENTS 4,797,480 A    1/1989    Sorbi et al.

FOREIGN PATENT DOCUMENTS

| JP | 2000-206116 | 7/2000 |
|---|---|---|
| JP | 2002-531810 | 9/2002 |

OTHER PUBLICATIONS

Deerinck, T.J. et al., Fluorescence Photooxidation with Eosin: A Method for High Resolution Immunolocalization and In Situ Hybridization Detection for Light and Electron Microscopy, Aug. 1994, pp. 901-910, The Journal of Cell Biology, vol. 126, No. 4.

(Continued)

*Primary Examiner*—Jezia Riley
(74) *Attorney, Agent, or Firm*—Morgan Lewis & Bockius

(57) ABSTRACT

The present invention provides a method of analyzing the physiological function of a target substance by inactivating the physiological function of the target substance, comprising the steps of: (a) binding to the target substance a photoactive compound represented by formula (I):

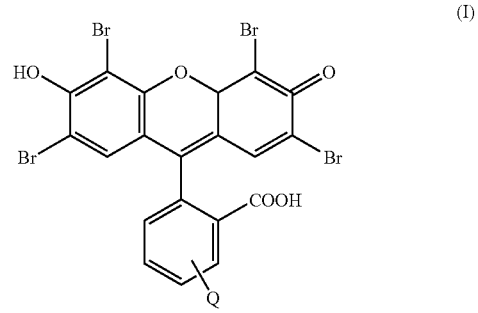

(in the formula, Q is a group for binding this compound with the target substance) to form a composite comprising the target substance and the photoactive compound; and (b) irradiating the obtained composite with light to inactivate the function of the target substance to which the photoactive compound has been bound, or to inactivate the function of the target substance at the site where the photoactive compound has been bound.

12 Claims, 1 Drawing Sheet

OTHER PUBLICATIONS

Giepmans, B.N.G. et al., The Fluorescent Toolbox for Assessing Protein Location and Function, Apr. 14, 2006, pp. 217-224, www.sciencemag.com, vol. 312.

Yan, P. et al., Fluorophore-Assisted Light Inactivation of Calmodulin Involves Singlet-Oxygen Mediated Cross-Linking and Methionine Oxidation, 2006, pp. 4736-4748, Biochemistry 2006, 45.

Anke et al., *Chromophore-Assisted Laser Inactivation of Cellular Proteins, Methods in Cell Biology*, vol. 44, 1994, 715-733.

Jay, *Selective Destruction of Protein Function by Chromophore-Assisted Laser Inactivation*, Proc. Natl. Acad. Sci., USA, vol. 85, Aug. 1988, 5454-5458.

Surrey, et al.; "Chromophore-assisted light inactivation and self-organization of microtubules and motors", Proc. Natl. Acad. Sci. USA, vol. 95, pp. 4293-4297, 1998.

METHOD OF ANALYZING PHYSIOLOGICAL FUNCTION OF TARGET SUBSTANCE

TECHNICAL FIELD

The present invention relates to a method of analyzing physiological function of a target substance by irradiating light to inactivate the physiological function of the target substance, and also relates to a photosensitive agent used in this analytical method.

BACKGROUND ART

In the past, chromophore-assisted light inactivation (CALI) was known as a method to analyze the function of a protein by spacio-temporally inactivating a functional site of a target protein and identifying the functional site of that protein or function thereof (refer to Japanese Patent Application Publication (tokukai) No. 2000-206116, and Japanese Patent Application Publication (tokuhyou) No. 2002-531810). These patent publications disclose that malachite green, rhodamine derivatives, and fluorescein derivatives, etc. can be used as the photosensitive agent in CALI. It is also known that fluorescein derivatives are more suitable than malachite green as a photosensitive agent to be used in CALI (refer to Proc. Nat. Acad. Sci. USA, Vol. 95, pp. 4293-4298, Apr. 1988 Biophysics). Then, it is known that, when using fluorescein as the photosensitive agent, singlet oxygen contributes to the functional destruction in the target site in the target protein (refer to Proteomics 2002, 2, 247-255).

Meanwhile, the production of singlet oxygen in a variety of fluorescein derivatives is described in Photochemistry and Photobiology, Vol. 37, No. 3, pp. 271-278, 1983.

As described in the publications above, malachite green and fluorescein were used in the past as photosensitive agents in order to spacio-temporally destroy biological functions dependent on irradiation with light. However, it was necessary either to use a large quantity of light irradiation or an extended irradiation time because the amount of active oxygen produced per unit light irradiation was small when using these substances. Consequently, when using conventional photosensitive agents, there was concern about photo-toxicity caused by the intense light irradiation itself, and biological function analysis research requiring high time resolution could not be conducted. For this reason, an analytical method was sought in which the spacio-temporal destruction of biological function could be achieved with shorter and weaker light irradiation.

DISCLOSURE OF THE INVENTION

The present invention was made to resolve the problems with the background art as described above. According to a first embodiment, the present invention provides a method of analyzing the physiological function of a target substance by inactivating the physiological function of the target substance, comprising the steps of:

(a) binding to the target substance a photoactive compound represented by formula (I):

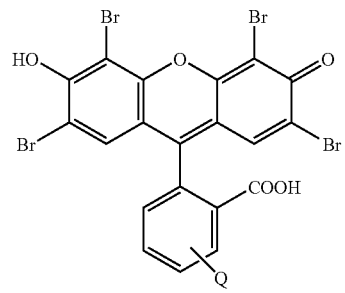

(in the formula, Q is a group for binding this compound with the target substance) to form a composite comprising the target substance and the photoactive compound; and (b) irradiating the obtained composite with light to inactivate the function of the target substance to which the photoactive compound has been bound, or to inactivate the function of the target substance at the site where the photoactive compound has been bound. The photoactive compound and the target substance are directly bound, or are bound through a partner substance that can bind to the target substance.

The compound in the aforementioned formula (I) is a photoactive compound wherein a group that can bind with the partner substance has been bound to tetrabromofluorescein (called "eosin" hereinafter), which is one of the fluorescein derivatives. It is known that many fluorescein derivatives can be used as the photosensitive agent, but the present inventors completed the present invention by discovering that among these fluorescein derivatives, eosin exhibits a quantity of singlet oxygen production greater than expected. As indicated in the examples to be described later, when actually measuring the singlet oxygen production activity of fluorescein and eosin using antracene-9,10-dipuropionic acid as a singlet oxygen probe, surprisingly, it was confirmed that despite having excited fluorescein at an optimum 488 nm, eosin produced about 2.5 times more per unit light irradiation than fluorescein. When actually binding β-galactosidase with a substance wherein antibodies to β-galactosidase were labeled with eosin, it was confirmed that the β-galactosidase activity was reduced approximately 3.5 times by irradiating with 515 nm light.

BEST MODE FOR CARRYING OUT THE INVENTION

Figure 1:
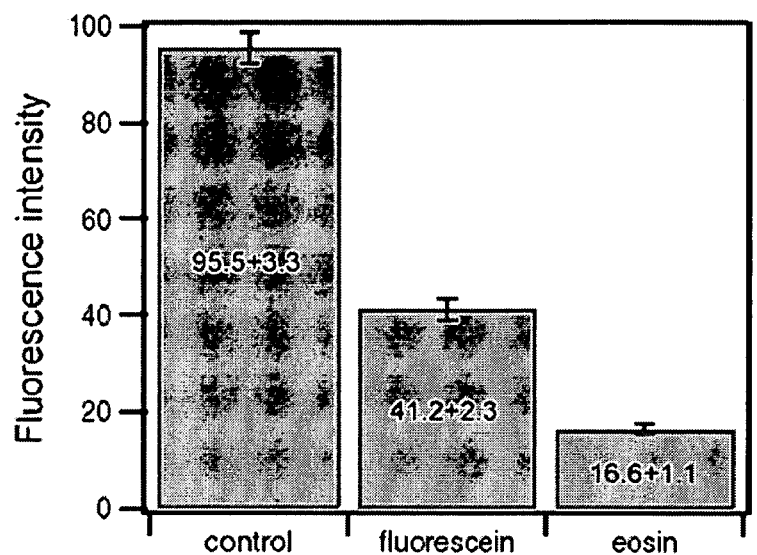
FIG. 1 indicates the fluorescent intensities of the samples irradiated with light in Example 1 when taking the fluorescent intensity of samples not irradiated with light to be 100%.

The present invention will be explained in detail below with reference to embodiments thereof.

A first embodiment of the present invention relates to a method to analyze the physiological function of a target substance by inactivating the physiological function of the target substance, comprising the steps of:

(a) binding to the target substance a photoactive compound represented by formula (I) directly or through a partner substance that can bind with the target substance to form a composite of the target substance and the photoactive compound, or a composite of the target substance and the partner substance, and (b) irradiating the obtained composite with light to inactivate the function of the target substance to which the photoactive compound has been bound, or to inactivate the function of the target substance at the site where the photoactive compound has been bound.

In a preferable embodiment of the present invention, in the aforementioned step (a), the photoactive compound represented by formula (I) is bound to the target substance through a partner substance for the target substance, to form a composite of the target substance, the partner substance, and the photoactive substance.

The compound of formula (I) is a compound wherein eosin, which is a photosensitive agent, is bound to a group "Q" for binding eosin to the target substance. Q is a group for directly binding eosin to the target substance or indirectly binding through a partner substance or the like to be described later. As long as this object is achieved, this compound is not particularly limited. For example, Q is -A-$Q^1$, wherein A is a chemical bond or a spacer group comprising 1 to 9 atoms (normally 1 to 6) selected from carbon, oxygen, and nitrogen in its chain, and $Q^1$ is a group selected from an isocyanate group, isothiocyanate group, sulfonyl chloride group, 4,6-dichlorotriazinyl amino group, maleimide group and iodine acetamide group. The spacer group "A" preferably is a chemical bond or alkylene of 1 to 6 carbon atoms (normally 2 to 4), —$CONHCH_2$—, —$NH(CONHCH_2$-)x, —$NHCS(NHCH_2CO)xNHCH_2$— (x is 1 through 3). Q is more suitably an isocyanate group, sulfonyl chloride group, or a maleimide group. Further, if the target substance has an amino group, Q may be selected, for example, from an isocyanate group, sulfonyl chloride group, or 4,6-dichlorotriazinyl amino group. Moreover, if the target substance has a mercapto group, Q may be selected, for example, from a maleimide group, or iodine acetamide group. Reference can be made to the descriptions, for example, in Japanese Patent Application Publication (tokukai) No. H5-310800 and Japanese Patent Application Publication (tokuhyo) No. H8-505121 for this kind of binding group or spacer group. Further, eosin and isothiocyanates thereof are well-known and commercially available. A person skilled in the art can synthesize an eosin derivative having the aforementioned substituent "Q" using well-known methods.

In the method of the present invention, the target substance is a biological molecule, of which the physiological functions are targeted for clarification. Although not particularly limited to these, examples include proteins, peptides, carbohydrates, lipids, DNA, RNA, sugars, and signal transducers. Specifically, the substances targeted by the method of the present invention are proteins; and enzymes, receptor proteins, ligand proteins, signal transducing proteins, transcriptional control proteins, skeletal proteins, cell adhesion proteins, and scaffold proteins may be cited as examples of suitable targets.

The partner substances using in the present invention are substances that can bind to the target substance that is the object of the method of the present invention. Partner substances used in the present invention are not particularly limited, but include antibodies, scFv, Fab, RNA, DNA, and other compounds that can bind to target proteins (for example, ligands that bind to receptors, substrates that bind to enzymes, and signal transducers that can bind to receptors such as inositol triphosphate). As disclosed in Japanese Patent Application Publication (kokai) No. 2000-206116, partner substances may be selected from combination libraries using such technologies as stage 1 selection (refer to the specification of DE19802576.9), phage display (Cwirla, S. E. et al. 1997, Science 273, 464-471) peptide on plasmid (Stricker, N. L. et al. 1997, Nature Biotechnology 15, 336-342) SIP (Spada, S. et al. 1997, Biol. Chem. 378, 445-456) CLAP (Malmborg, A.-C. et al. 1997, JMB 273, 544-551) ribosome/polysome display (Kawasaki, G. 1991, International Patent Application WO91/05058 Description; Hanes, J. & Pluckthun, A. 1997, PNAS 94, 4937-4942) or SELEX (Tuerk, C. & Gold, L. 1990, Science 249, 505-510). Examples of this kind of library may include protein libraries, peptide libraries, cDNA libraries, mRNA libraries, libraries with organic molecules, scFv libraries with immunoglobulin super-families, and protein display libraries. Further, in a preferred embodiment, the aforementioned target substance is a protein such as an enzyme, and the aforementioned partner substance is Fab, scFv or an antibody that can bind with that protein.

In the aforementioned step (a), the aforementioned kind of photoactive compound (L) is bound to a target substance (T), which, for example, is a protein, through a partner substance (P) bound to the target substance, for example through an antibody, to form a bound composite (L-P-T) of these. This kind of composite (L-P-T) may be formed by binding the partner substance (P) with the photoactive substance (L), and then binding the target substance (T) to this, or may be formed by binding the partner substance (P) with the target substance (T), and then binding the photoactive substance (L) to this.

In addition, in the aforementioned step (a), the photoactive compound may be directly bound to the target protein. In this case, a 4 base codon or a 5 base codon may be utilized as the method to introduce onto the specified site of the target protein a non-natural amino acid having the photoactive compound on a side chain (refer to T. Hohsaka, Biochemistry 2001, 40, pp. 11060-11064). In this case, the previously described spacer group "A" may be present between the photoactive compound and the Cα of the amino acid having that compound on a side chain.

This composite is formed under conditions such that the physiological function of the target substance is not harmed. These conditions may be suitably and individually set by a person skilled in the art who understands the properties of the target substance and the partner substance. For example, if the target substance is a protein, both may come into contact under the condition that the protein is not de-natured when forming the composite. Preferably, that condition applies to the physiological conditions of the cell environment of the target protein.

Next, in the aforementioned step (b), the obtained composite is irradiated with light using CALI technology, to directly and specifically inactivate the target substance to which the photoactive compound has been bound, or the function of the target protein at the site to which the photoactive compound has been bound (refer to PNAS, 85, 5454-545 8, 1988; Trends in Cell Biology, 6, 442-445, 1996). Specifically, when irradiating with light having a wavelength of 480 to 540 nm, which is the absorption wavelength of the photoactive compound of the present invention, this light is absorbed by the photoactive compound to produce singlet oxygen, resulting in inactivation of the target substance (for example, a protein), or a functional site thereof, bound to the photosensitive agent in a radius of approximately 10 to 50 Å. Further, the maximum absorption of eosin (max λ) in water is 517 nm, and 523 nm in ethanol (refer to Photochemistry and Photobiology, Vol. 37, No. 3, pp. 271-278, 1983). The amount of irradiation necessary for inactivation is, for example, from 0.1 W/$cm^2$ to 10 W/$cm^2$, preferably from 0.5 to 2 4W/cm2. Although not particularly limited to this, the type of irradiated light may, for example, be from a xenon arc light, mercury arc light, halogen lamp, tungsten lamp, color laser, argon laser (wavelength 488 or 514.5 nm lines), or double frequency Nd:YAG laser (532 nm).

The physiological function of that target substance can be analyzed by inactivating the target substance itself or a specified site of the target substance in this way. For example, based on this kind of inactivation it is possible to assay the functional site of the protein, confirm the function of that functional site, confirm ligand function, confirm the affect of the functional site on the longevity of the protein, and confirm the affect of the functional site on protein folding, etc. Further, the analytical method of the present invention can be used in in vitro and in vivo assays as well as analysis of target molecules present inside and outside the cell.

For example, identification of the functional site of the inactivated protein can be achieved by fragmenting the inactivated protein and subjecting the fragments to mass spectrometry measurement as described in Japanese Patent Application Publication (tokuhyo) No. 2002-531810.

More specifically, the inactivated protein is fragmented using a protease that cleaves at a specific position. Examples of this kind of protease include trypsin, chymotrypsin, and papain. Chemical cleavage of proteins may be conducted, for example, by cyan bromide (specific to Met), 3-bromo-3-methyl-2-(2-nitrophenyl mercapto)-3H-indol (BNPS-skatole; specific to Trp), 2-nitro-5-thiocyanate benzoate (specific to Cys), and Fe-EDTA.

The cleaved fragment mixture is separated by electrophoresis, and then the inactivated site can be specified by conducting mass spectrometry and comparing with untreated target protein. When using CALI to inactivate the target protein, the denatured amino acid of the inactivated protein participating in inactivation can be immediately specified by tandem mass spectrometry (refer to Rapid Commun. Mass Spectrom., 11, 1015-1024, 1997; Rapid Commun. Mass Spectrom., 11, 1067-1075, 1997). The analysis by mass spectrometry may be conducted by a variety of well-known methods, for example, by using an electron spray ionized source (Chapman, J. R., et al., Methods in Molecular biology, 61, J R Chapman editor, Humana Press Inv. Totowa N.J., USA, 1996) including nano-electron spray (Wilm. M. and Mann, M., Anal. Chem. 68, 1-8, 1996) and matrix-assisted laser desorption/ionization (MALDI) (Siuzdak, G. Mass Spectrometry for Biotechnology, Academic Press Inc. 1996), or by using a combination of mass analyses such as triple, quadruple pole, time-of-flight, magnetic sector, Fourier conversion ion cyclotron resonance, and quadruple pole ion trapping.

In addition, reference can be made to the description in Japanese Patent Application Publication (tokuhyo) No. 2002-531810 for the details of the aforementioned analytical methods or of the equipment to automate the same.

Moreover, described in Japanese Unexamined Patent Application Publication No. 2000-206116 is a method to confirm the function of a target ligand using CALI technology, and the method of the present invention can be applied to this kind of ligand function confirmation method.

Further, the photosensitive agent related to the present invention efficiently produces singlet oxygen, and therefore application as a therapeutic drug for photodynamic therapy may also be considered (refer to Japanese Patent Application Publication (tokuhyo) No. 2000-500741).

EXAMPLES

The present invention will be explained more specifically below with reference to working examples.

Example 1

Comparison of the Amount of Singlet Oxygen Produced

Antracene-9,10-dipuropionic acid (molecular probe) and each of colorants (eosin, fluorescein) were dissolved in PBS (−) to make 100 μM respectively, and 100 μL was taken. The structural formulae of the colorants will be indicated next as a reference.

Then, 20 μL each of the samples obtained were filled into two wells of a Terasaki plate (Nalge Nunc), and one sample was irradiated for 60 seconds with 2 W/cm$^2$ 488 nm laser light (sapphire, coherent). 300 μL of PBS(−) was added to the light irradiated samples and the non-irradiated samples, respectively. The samples were transferred to a quartz glass cuvette, and the 430 nm fluorescence emission based on 380 nm excitation was measured using a fluorophotometer (Hitachi). In addition, antracene-9,10-dipuropionic acid emits fluorescence of a maximum peak of 430 nm when excited by 380 nm, but has no fluorescent properties when oxidized by singlet oxygen. The measurement of singlet oxygen is based on this principle.

The results obtained in this way are indicated in FIG. 1. Further, the graph indicated in FIG. 1 shows the fluorescent intensities of the samples irradiated with light when taking the fluorescent intensity of a sample not irradiated with light as 100%. Samples that did not contain colorant were used as a contrast (control). The same experiment was conducted three times, and the mean values and standard error were calculated. As indicated in FIG. 1, it was confirmed that despite exciting fluorescein with the optimum 488 nm, eosin produced singlet oxygen 2.5 times more efficiently compared to fluorescein.

Example 1 and Comparative Example 1

Inactivation of β-Galactosidase

After dissolving anti-β-galactosidase antibody in 0.5M sodium hydrogen carbonate solution (pH 9.5) to make a concentration of 80 μg/mL, 40 μg/mL of eosin isothiocyanate (EITC: molecular probe; Example 1) or fluorescein isothiocyanate (FITC: molecular probe; Comparative Example 1) was added, shaded and incubated for 30 minutes. The samples were gel filtered using a PD-10 pre-pack column (Amasham Pharmacia Biotech), and colorant labeled samples were recovered. Anti-rabbit IgG antibody was also labeled in the same way using FITC. 15 μL each of PBS(−) solutions containing β-galactosidase (10 μg/mL), colorant labeled anti-β-galactosidase antibody (200 μg/mL), and BSA (120 μg/mL) were filled into 2 wells of a Takasaki plate (Nalge Nunc), and one sample was irradiated for 60 seconds with 2 W/cm$^2$ 488 nm laser light (sapphire, coherent).

Figure 2:
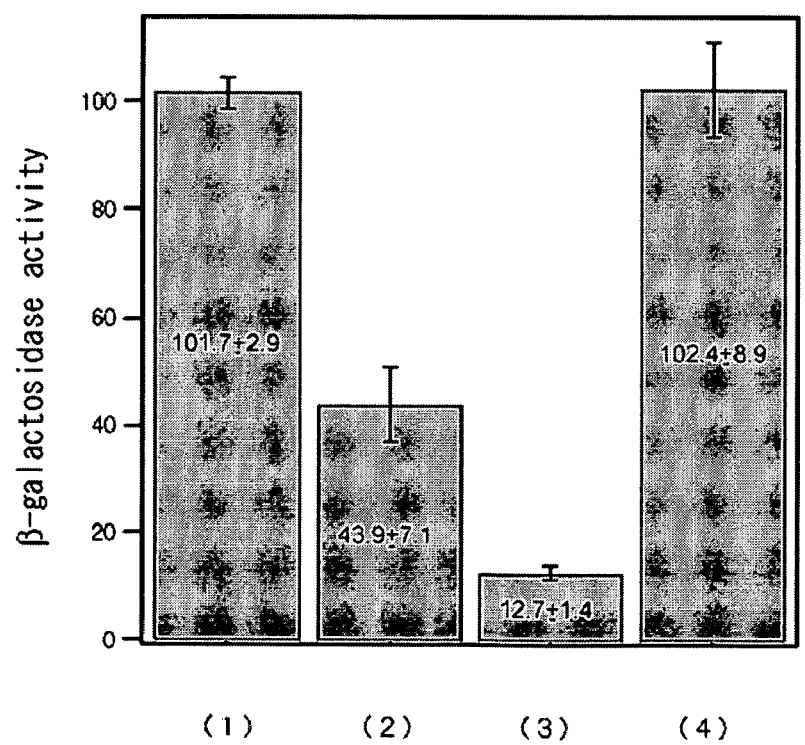
FIG. 2 indicates the β-galactosidase activities of samples irradiated with light in Example 1 and Comparative Example 1 when taking the β-galactosidase activity of samples not irradiated with light to be 100%.

The β-galactosidase activity was measured using a β-galactosidase enzyme assay system (Promega) that uses reporter lysis buffer. Anti-β-galactosidase antibody not labeled with colorant and fluorescein labeled anti-rabbit IgG antibody were used as controls. The same experiment was conducted three times, and the mean value and standard error were calculated. The results obtained are indicated in FIG. 2. The graph indicated in FIG. 2 shows the β-galactosidase activity of the samples irradiated with light when taking the β-galactosidase activity of the samples not irradiated with light as the 100%. Further, indicated in the diagram is the β-galactosidase activity of: (1) anti-β-galactosidase antibody, (2) fluorescein labeled anti-β-galactosidase antibody, (3) eosin labeled anti-β-galactosidase antibody, and (4) fluorescein labeled anti-rabbit IgG antibody.

As demonstrated in the graph indicated in FIG. 2, it was confirmed that the β-galactosidase activity of β-galactosidase bound with eosin labeled anti-β-galactosidase antibody (Example 1) was reduced approximately 3.5 times compared to when labeled with fluorescein (Comparative Example 1).

INDUSTRIAL APPLICABILITY

As explained above, the present invention provides a method, and a photosensitive agent using that method, to improve the analysis of the physiological functions of a target substance by inactivating the physiological function of the target substance by irradiating with light. The method of the present invention has the advantage that there is no concern about photo-toxicity compared to conventional methods because irradiation of light for a short time or irradiation of light of a weak intensity is sufficient. Moreover, there is also the advantage that the method of the present invention can be effectively used in physiological function analysis research requiring high time resolution.

In the claims:

1. A method of analyzing the physiological function of a target by inactivating said target, comprising the steps of:
   (a) binding to the target a photoactive compound represented by formula (I):

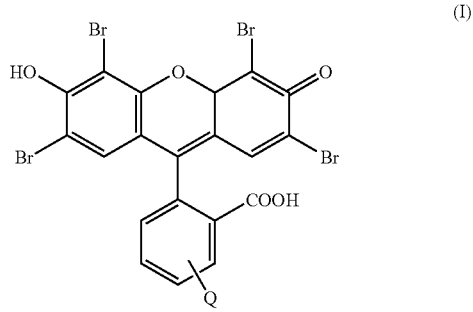

to form a composite comprising the target and the photoactive compound,
in the formula, Q is a group for directly binding this compound with the target or indirectly binding through a partner substance, wherein Q is a group that can bind with the partner substance and is represented by -A-$Q^1$; wherein A is a chemical bond or a spacer group comprising 1 to 9 atoms selected from carbon, oxygen, and nitrogen in its chain, and $Q^1$ is a group selected from an isocyanate group, isothiocyanate group, sulfonyl chloride group, 4,6-dichlorotiazinyl amino group, maleimide group and iodine acetamide group; and
   (b) irradiating the obtained composite with light using a xenon arc light, mercury arc light, halogen lamp, tungsten lamp, color laser, argon laser having wavelength 488 or 514.5 nm lines, or double frequency Nd:YAG laser having wavelength 532 nm to inactivate the function of the target to which the photoactive compound has been bound, or to inactivate the function of the target at the site where the photoactive compound has been bound, thereby analyzing the physiological function of the target, wherein the amount of irradiation necessary for inactivation is from 0.1 W/cm² to 10 W/cm².

2. The method according to claim 1, wherein the binding of the photoactive compound and the target is conducted through a partner substance that can bind with the target.

3. The method according to claim 1, wherein the target is selected from proteins, peptides, carbohydrates, lipids, DNA, RNA, sugars, and signal transducers.

4. The method according to claim 1, wherein the partner substance is selected from antibodies, scFv, Fab, RNA, DNA, proteins, peptides, carbohydrates, sugars, lipids, ligands, and signal transducers.

5. The method according to claim 1, wherein the target is a protein, and the partner substance is an antibody, scFv or Fab.

6. The method according to claim 1, wherein the amount of irradiation necessary for inactivation is from 0.5 W/cm² to 2 W/cm².

7. A method of analyzing the physiological function of a target by inactivating said target, comprising the steps of:
   (a) binding to the target a photoactive compound represented by formula (I):

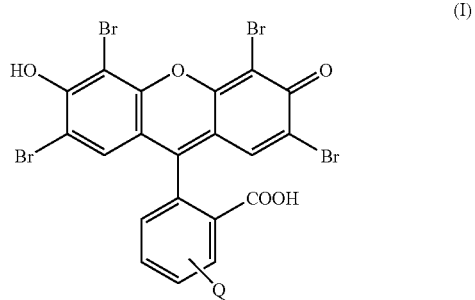

to form a composite comprising the target and the photoactive compound,
in the formula, Q is a group for directly binding this compound with the target or indirectly binding through a partner substance, wherein Q is an isothiocyanate group, sulfonyl chloride group, or maleimide group; and
   (b) irradiating the obtained composite with light using a xenon arc light, mercury arc light, halogen lamp, tungsten lamp, color laser, argon laser having wavelength 488 or 514.5 nm lines, or double frequency Nd:YAG laser having wavelength 532 nm to inactivate the function of the target to which the photoactive compound has been bound, or to inactivate the function of the target at the site where the photoactive compound has been bound, thereby analyzing the physiological function of the target, wherein the amount of irradiation necessary for inactivation is from 0.1 W/cm² to 10 W/cm².

8. The method according to claim 7, wherein the binding of the photoactive compound and the target is conducted through a partner substance that can bind with the target.

9. The method according to claim 7, wherein the target is selected from proteins, peptides, carbohydrates, lipids, DNA, RNA, sugars, and signal transducers.

10. The method according to claim 7, wherein the partner substance is selected from antibodies, scFv, Fab, RNA, DNA, proteins, peptides, carbohydrates, sugars, lipids, ligands, and signal transducers.

11. The method according to claim 7, wherein the target is a protein, and the partner substance is an antibody, scFv or Fab.

12. The method according to claim 7, wherein the amount of irradiation necessary for inactivation is from 0.5 W/cm² to 2 W/cm².

* * * * *